(12) United States Patent
Vesely

(10) Patent No.: US 6,569,196 B1
(45) Date of Patent: May 27, 2003

(54) SYSTEM FOR MINIMALLY INVASIVE INSERTION OF A BIOPROSTHETIC HEART VALVE

(75) Inventor: Ivan Vesely, Cleveland Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/597,918

(22) Filed: Jun. 19, 2000

Related U.S. Application Data

(63) Continuation of application No. PCT/US98/27481, filed on Dec. 23, 1998.
(60) Provisional application No. 60/068,711, filed on Dec. 29, 1997.

(51) Int. Cl.$^7$ ................... A61F 2/24; A61F 2/06
(52) U.S. Cl. ................ 623/2.14; 623/1.24; 623/1.26
(58) Field of Search ................. 623/2.12, 2.13, 623/2.17, 1.26, 1.24, 1.25

(56) References Cited

U.S. PATENT DOCUMENTS

| | | | |
|---|---|---|---|
| 3,898,701 A | * 8/1975 | La Russa | 623/2.11 |
| 4,056,854 A | 11/1977 | Boretos et al. | 3/1.5 |
| 4,506,394 A | 3/1985 | Bedard | 3/1.5 |
| 4,680,031 A | * 7/1987 | Alonso | 623/2 |
| 4,790,843 A | * 12/1988 | Carpentier et al. | 623/2 |
| 5,312,360 A | 5/1994 | Behl | 604/164 |
| 5,411,552 A | 5/1995 | Andersen et al. | 623/2 |
| 5,545,214 A | 8/1996 | Stevens | 623/2 |
| 5,554,185 A | 9/1996 | Block et al. | 623/2 |
| 5,571,174 A | 11/1996 | Love et al. | 623/2 |
| 5,593,424 A | 1/1997 | Northrup, III | 606/232 |
| 5,607,446 A | 3/1997 | Beehler et al. | 606/198 |
| 5,662,676 A | 9/1997 | Koninckx | 606/198 |
| 5,718,725 A | 2/1998 | Sterman et al. | 623/2 |
| 5,807,405 A | 9/1998 | Vanney et al. | 623/112 |
| 5,843,181 A | 12/1998 | Jaffe et al. | 623/2 |
| 5,855,601 A | 1/1999 | Bessler et al. | 623/2 |
| 5,910,170 A | 6/1999 | Reimink et al. | 623/2 |
| 5,957,949 A | 9/1999 | Leonhardt et al. | 606/194 |
| 6,106,550 A | 8/2000 | Magovern et al. | 623/2.38 |
| 6,168,614 B1 | 1/2001 | Andersen et al. | 623/1 |
| 6,197,054 B1 | 3/2001 | Hamblin, Jr. et al. | 623/2.38 |
| 6,312,465 B1 | 11/2001 | Griffin et al. | 623/2.38 |

FOREIGN PATENT DOCUMENTS

WO 99/33414 7/1999

* cited by examiner

*Primary Examiner*—Corrine McDermott
*Assistant Examiner*—Alvin Stewart
(74) *Attorney, Agent, or Firm*—Mark Kusner; Michael A. Jaffe

(57) ABSTRACT

A system for minimally invasive insertion of a bioprosthetic heart valve. The system includes a collapsible tissue-based valve system, a catheter-based valve delivery system, a surgical platform and a device tracking and visualization system. The collapsible valve system includes: (i) a permanent outer frame (10) that is affixed to the patient using conventional sutures or staples, and (ii) a collapsible valve (20) having a collapsible inner frame (21) that mates with the outer frame (10), and supports valve leaflets (13). The inner frame (21) is moved to a collapsed position and located at the previously installed outer frame (10). The inner frame (21) is then expanded to lock the inner frame (21) to the outer frame (10). The inner frame (21) may be re-collapsed and disengaged from the outer frame (10). A new collapsible valve (20) is then installed, to resume the function of the prosthesis.

17 Claims, 7 Drawing Sheets

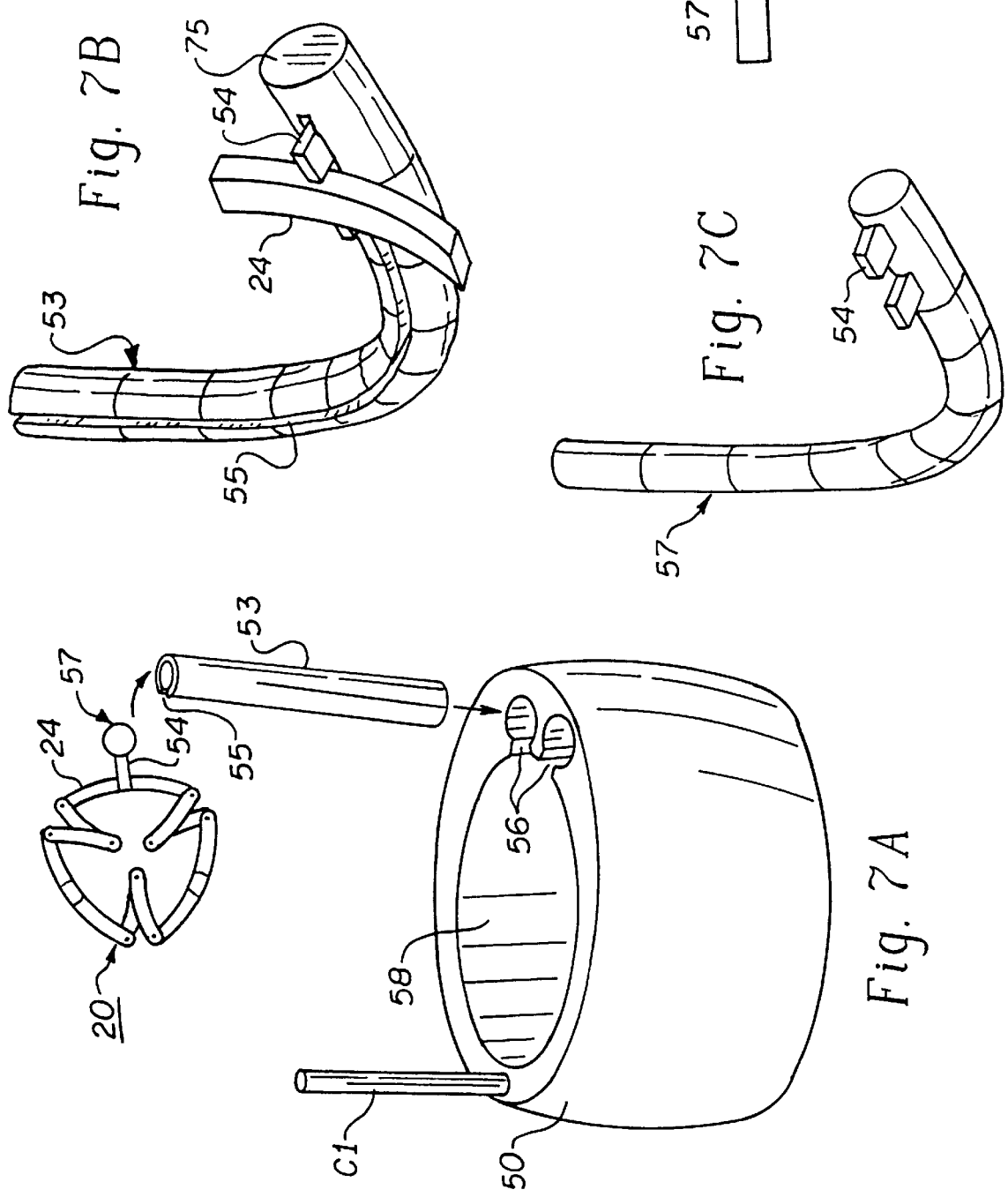

SYSTEM FOR MINIMALLY INVASIVE INSERTION OF A BIOPROSTHETIC HEART VALVE

RELATED APPLICATION

This is a continuation of International Application PCT/US98/27481, with an international filing date of Dec. 23, 1998, and claims the benefit of a provisional application No. 60/068,711, filed Dec. 29, 1997.

BACKGROUND OF THE INVENTION

The current practice of inserting artificial heart valves involves cutting the chest open, placing the patient on cardiopulmonary bypass, and surgically inserting the valve into an aorta. This process can take several hours and subjects the patient to significant operative mortality. While the mortality during first valve replacement surgery can be very low (less than 5%), the second surgery carries much greater operative mortality, and the third is even more risky (>15%). Consequently, first and second re-operations to replace a worn out bioprosthetic heart valve are avoided. Since a typical bioprosthesis, or tissue valve, can wear out in 10 years, these valves are typically implanted into patients 60 years old, or older. Younger patients are often recommended a mechanical valve that does not wear out, and typically does not need replacement.

Tissue valves, however, are often preferred over mechanical valves because of their better biocompatibility. Mechanical valves cause blood to clot on their components, and the patient must therefore be chronically treated with anticoagulants to eliminate the risk of major blood clots. Anticoagulant themselves, however, carry a measurable risk of bleeding and thromboembolism and are not an ideal solution. Because tissue valves do not need to be anticoagulated, they are potentially the ideal valve prosthesis, if only their durability were to be improved.

Accordingly, the goal of most tissue valve research and development, has been the improvement in valve durability so that these tissue valves can be put into patients younger than 60 or 65. Because of the operative mortality and morbidity, the objectives of all valve research and development, has been to increase the functional life span of the bioprosthesis so that it can be put into patients only once, and will last the life of the patient. This has thus far been an extremely difficult goal to reach.

There may be another option, however, for the use of tissue heart valves in the younger population. Rather than building valves that last longer, it may be more appropriate to build valves that can be routinely replaced in a way that induces negligible patient morbidity. The objectives would therefore be not to have extremely durable valves, but rather valves that can be easily removed when they begin to fail and new ones inserted. The technologies that make this possible already exist with the advances made in the field of catheter-based endovascular procedures, and the more broad field of Minimally Invasive Surgery (MIS).

The field of MIS is growing at an accelerating pace. The approach involves the use of small surgical probes, cannulas, video cameras and remote staplers and suture drivers that enable surgery to be done without requiring large incisions. Most MIS is done with several small incisions, simply to allow the passage of these instruments into the patients body. The principal advantages of MIS is that the patient is subjected to less surgical trauma and has a dramatically reduced hospital stay, which in turn significantly reduces the operating costs of the clinical center.

Current generation minimally invasive procedures are being carried out using endoscopes and long-reaching surgical tools. Typically, the patient's abdomen is inflated with carbon dioxide and the instruments are inserted through small incisions. The surgeons then perform the procedures using endoscopic visualization. For cardiothoracic surgery, similar small incisions are created between the ribs and the heart is placed on bypass using multiple cannulas with balloons that can selectively shut off blood flow through the heart, and direct it through oxygenators.

Other technologies are being developed to do surgery on beating hearts, as to completely avoid placing the heart on bypass. Many of these procedures involve the use of specialized catheters that deploy devices or tools that perform a wide range of procedures on the beating heart. Typical beating heart procedures are endovascular balloon dilatation of arteries and stent placement. Deployment of stents and other permanent devices has become commonplace, but to date, no successful, catheter deployable valve has been developed.

While U.S. Pat. No. 5,545,214 discloses a balloon-deployable tissue valve, the technology is similar to that of stents, and is not ideal for tissue heart valves. The material that anchors the valve in the patient=s aortic root is permanently deformed through the bending of metal components, and is not intended to be re-collapsed into its original configuration. Practically the same approach is disclosed in U.S. Pat. No. 5,411,552. U.S. Pat. No. 5,554,185 discloses a means of deploying the valve by inflating of a hollow valve frame with a liquid that hardens. U.S. Pat. No. 5,545,209 describes the use of balloon technology to permanently distend and deploy an endoprosthesis, typically a vascular segment for treating abdominal aneurysm. This patent makes reference to "a tubular prosthesis disposed on said catheter over at least a portion of said balloon." The major concepts disclosed by all of these patents are similar: the permanent deployment of a bioprosthetic heart valve. A permanently deployed tissue heart valve, whether it is done using MIS technology or not, is subject to the same requirements as conventional tissue valves: it must be very durable. Good durability, however, is not easily attained. The manufacturing process of tissue heart valves is very mature and complex from the quality control point of view, and only minimal improvements in valve durability have been achieved in recent years. Major improvements in valve durability are therefore not expected in the near future.

The present invention addresses the drawbacks discussed above, as well as other problems encountered with the prior art, to provide a system for minimally invasive removal and re-insertion of a bioprosthetic heart valve. One key feature of the present invention is a valve that can be collapsed after many years of use in the patient. The collapsing or expanding process does not involve any permanent deformation of components, as has been required for the systems disclosed in the preceding patents. A properly collapsible valve is first removed from the patient using catheters, when it has failed to provide proper function to the patient, a new version of the same temporary collapsible valve is inserted using the same catheter technology.

SUMMARY OF THE INVENTION

According to the present invention there is provided a system for minimally invasive removal and re-insertion of a bioprosthetic heart valve. Broadly stated, the device is sufficiently collapsible so as to be able to pass through the lumen of a catheter inserted into the femoral artery, or other large vessel. The collapsed valve is re-expanded when in place in order to fit into a permanent housing in the patients heart and assumes a fully functioning state. Integral to this system of removal and replacement of a prosthetic heart valve is an expandable "operative platform" that is deployed near the site of the valve so that it stabilizes the catheters and other instruments during the valve removal and reinsertion process.

In accordance with a first aspect of the present invention, there is provided a two component valve system comprised of a permanent housing which remains in the patient, and a collapsible valve which is replaced when it becomes necessary.

In accordance with a further aspect of the present invention, there is provided a permanent housing with an integrated sewing ring which is affixed to the patient aorta or other tissue by means of sutures or staples.

In accordance with another aspect of the present invention, there is provided a collapsible inner frame onto which several leaflets or flexible occluders are affixed, comprised of several articulating or hinged components which have a substantially smaller perimeter when fully collapsed, than when fully expanded.

In accordance with still another aspect of the present invention, there is provided an inflatable or distensible "surgical platform" which can be delivered to a site near the heart in a collapsed state and distended at that site such that it anchors the numerous catheters and devices in space thereby ensuring proper controlled manipulation of their distal ends, when acted upon by controls at their proximal ends.

In accordance with still another aspect of the present invention, there is provided an integrated check valve within the surgical platform that enables controlled ejection of blood from the ventricle during the process of collapsible valve removal and replacement.

In accordance with yet another aspect of the present invention, there is provided a split wall or "monorail" catheter system which can guide larger instruments and devices between the outside of the patient and the surgical platform during the course of a valve replacement procedure.

In accordance with yet another aspect of the present invention, there is provided a tracking and visualization system that can generate accurate images or graphical representation of the catheters and other components on a computer screen so as to accurately represent the position of the real components inside the body of the patient.

Although the prosthetic collapsible valve of the present invention may incorporate various number of leaflets, a preferred embodiment of the valve incorporates three (3) valve leaflets.

Although the collapsible valve of the present invention may incorporate a wide range of leaflet materials, such as synthetic leaflets or those constructed from animal tissues, a preferred embodiment of the valve incorporates three (3) valve leaflets constructed from sheets of chemically preserved bovine pericardium.

Although the permanent outer frame of the prosthetic cardiac valve of the present invention may be constructed from a wide range of materials including metals and plastics, a preferred embodiment of the outer frame is constructed from stiff, rigid metal such as stainless steel.

Although the collapsing mechanism of the collapsible valve of the present invention may incorporate various means of remaining permanently expanded within the permanent outer frame, a preferred embodiment of maintaining the collapsible valve in its expanded state is by means of precision machining of the components of the inner frame so that a "snapping" action holds them in their expanded position by means of an interference fit between components.

Although the collapsible valve of the present invention may be collapsed by various means, a preferred embodiment of the valve collapsing means incorporates one or more projections or "handles" that protrude from the collapsible frame so that they can be grabbed by a catheter-based snare means.

Although the collapsible valve of the present invention may be expanded by various means, a preferred embodiment of the valve expanding means incorporates an articulating expanding means that does not require the use of balloon technology to expand the collapsible frame.

Although the system for minimally invasive insertion of a collapsible valve may make use of numerous means of stabilizing the proximal ends of the catheters, a preferred embodiment of the procedure is the use of a stabilizing surgical platform that can be anchored distal to the aortic valve. The surgical platform incorporates slots and fixtures for attaching and holding catheters in slots that stabilize the movement and position of the distal ends of the catheters so that deflection and manipulation of the catheter ends is done in a controlled way.

Although the system for minimally invasive insertion of a collapsible valve may make use of numerous means of temporarily augmenting the action of the contracting heart by means of valves, a preferred embodiment of the procedure is the incorporation of an integrated check valve within the surgical platform that becomes functional once the platform is expanded in place. The integrated check valve can be fabricated out of polymer and have one or more occluding leaflets. The leaflets are soft and pliable and enable the passage of catheters and other devices past and through the leaflets.

Although the system for minimally invasive insertion of a collapsible valve may make use of numerous catheters to deliver the components of the collapsible valve system into the desired site, a preferred embodiment of the procedure is the use of a "monorail" or slotted catheter sheath that enables larger devices to be guided along the outside of the slotted catheter sheath to the operative site.

Although the system for minimally invasive insertion of a collapsible valve may make use of numerous imaging or visualization techniques, a preferred embodiment of the procedure is the use of a ultrasonic or electromagnetic sensors affixed to the catheters and components such that their position can be detected and tracked in 3-D space, in sufficient spatial and temporal resolution and precision, so as to make the procedure easy and accurate.

As can be seen by those skilled in the art, an advantage of the present invention is the provision of a valve system that allows for safe and convenient removal and replacement of a collapsible valve when it begins to fail.

Another advantage of the present invention is the provision of an expandable, re-collapsible tissue-based heart valve.

Yet another advantage of the present invention is the provision of a catheter-based valve delivery system.

Still another advantage of the present invention is the provision of a stable surgical platform within which catheter-based manipulators can be securely anchored so that intracardiac procedures can be properly executed.

Another advantage of the present invention is the provision of a synthetic valve integrated with the surgical platform to act as a temporary check-valve while the expandable, re-collapsible tissue-based heart valve is being replaced.

Yet another advantage of the present invention is the provision of a slotted catheter sheath that can act as a "monorail" guide to shuttle components along the outside of the sheath between the exit/entry port of the patient and the surgical platform within the heart.

Yet another advantage of the present invention is the provision of a ultrasound or electromagnetic catheter guidance system that can track the position and motion of the catheters and devices during the procedure and display images of the system components on a video display monitor, so as to make the procedure easy and accurate.

Still other advantages of the invention will become apparent to those skilled in the art upon a reading and understanding of the following detailed description, and accompanying drawings.

BRIEF DESCRIPTION OF THE DRAWINGS

The invention may take physical form in certain parts and arrangements of parts, a preferred embodiment and method of which will be described in detail in this specification and illustrated in the accompanying drawings which form a part hereof, and wherein:

FIG. 7A shows an exploded view of a catheter-based valve delivery system, including a surgical platform and numerous accessory devices and catheters, according to one preferred embodiment of the present invention;

FIG. 7B shows an enlarged partial sectional view of a slotted catheter sheath, according to a preferred embodiment of the present invention;

FIG. 7C shows an enlarged partial sectional view of an inner catheter, according to a preferred embodiment of the present invention;

FIG. 7D is a schematic representation illustrating the operation of gripping means, in accordance with a preferred embodiment of the present invention;

DETAILED DESCRIPTION OF THE PREFERRED EMBODIMENT

The detailed description set forth below in connection with the appended drawings is intended merely as a description of the presently preferred embodiment of the invention, and is not intended to represent the only form in which the present invention can be constructed or used. The description sets forth the function and sequence of steps for construction and implementation of the invention. It is to be understood that the same or equivalent functions and sequences may be accomplished by different embodiments that are also intended to be encompassed within the spirit and scope of the invention. For example, a similar system can be used to insert a similar collapsible valve (e.g., a prosthetic valve or endoprosthesis) into the mitral position, the pulmonary and tricuspid positions of the heart or an other expandable prosthetic device into any other location within the vasculature or an organ of any patient.

In accordance with a preferred embodiment of the present invention, a system for inserting a valve into the aortic position using a catheter-based, endovascular, minimally invasive techniques is generally comprised of the following:

(1) A valve that can be collapsed for insertion, expanded when in place so as it fits securely within a permanent housing that remains in the patient, and collapsed again for removal once the tissue component of the collapsible valve wears out.

(2) A multi-component, catheter-based system for the percutaneous, or MIS removal and delivery of the collapsible valve.

(3) A device tracking, visualization system to enable this procedure to be done with high precision and minimal chance of complications.

I. Construction of the Collapsible Cardiac Valve and Frame

Figure 1:
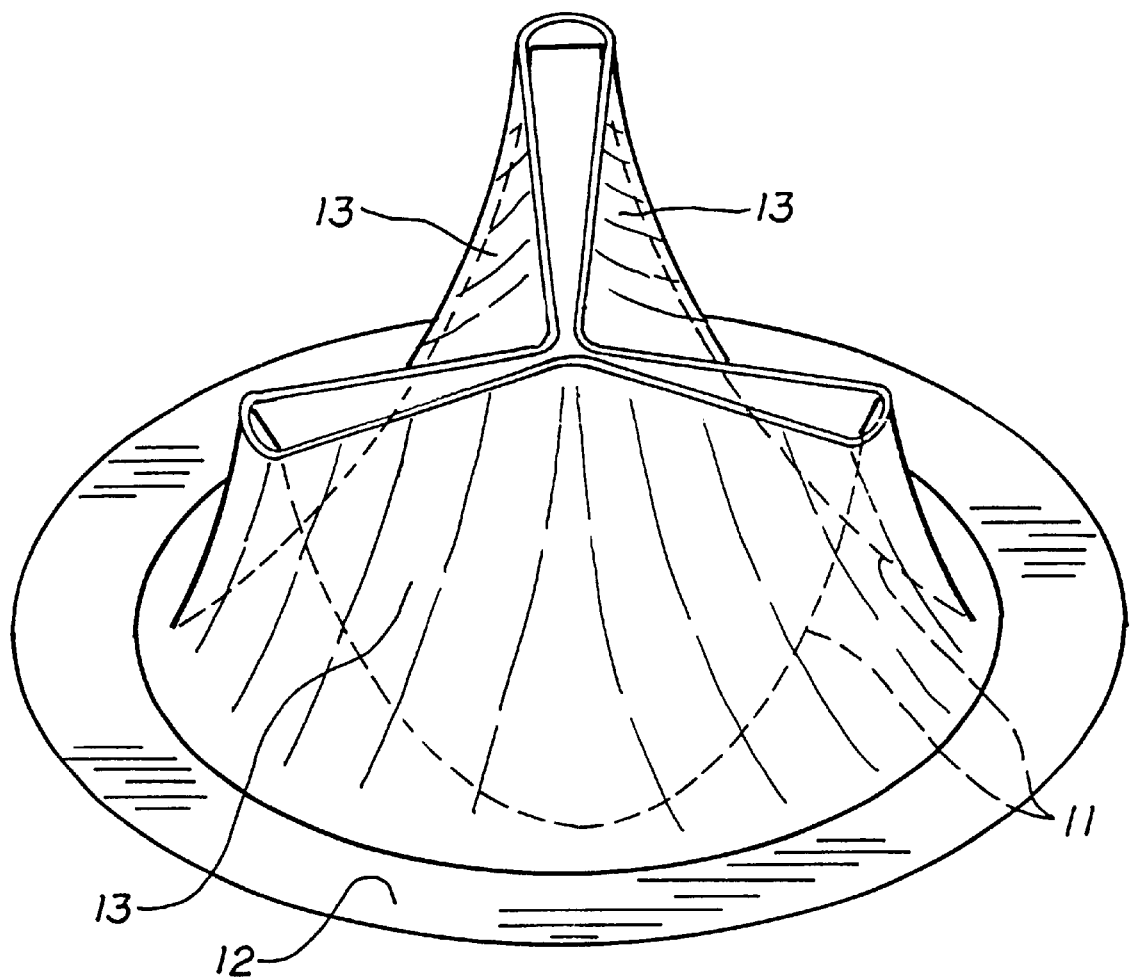
FIG. 1 shows images of typical prior art bioprosthetic valve having leaflets made of bovine pericardium mounted on a supporting stent.

One aspect of the present invention is directed to an expandable, re-collapsible tissue-based valve system. With reference to FIG. 1. a typical prior art tissue-based prosthetic valve includes three (3) leaflets 13 sewn to and supported on a metal or polymer frame or stent 11. One aspect of the present invention is directed to a collapsible valve system generally comprised of two components: (i) a permanent outer frame that is affixed to the patient using conventional sutures or staples (FIG. 2), and (ii) an inner collapsible valve (FIGS. 3A–3C and 4A–4B) that mates with the outer frame and includes valve leaflets. The inner collapsible valve is normally collapsed, is delivered against the previously inserted outer frame, expanded, and locked in place. Importantly, the inner collapsible valve may be collapsed again and removed. A new inner collapsible valve is then inserted into the original outer frame, to resume the function of the prosthesis.

Figure 2:
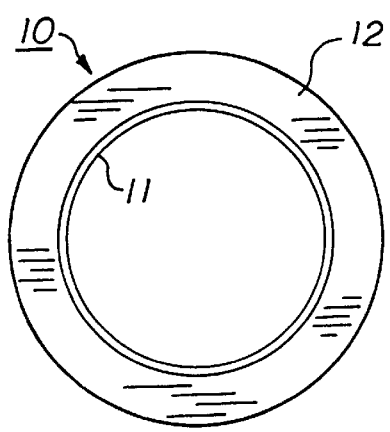
FIG. 2 shows a top plan view of the permanent outer frame, according to a preferred embodiment of the present invention.

With reference to FIG. 2, there is shown a preferred embodiment of the outer frame 10. Outer frame 10 is generally comprised of a rigid ring 11, and a soft sewing ring 12 for attachment of the outer frame 10 the wall of the aorta or other structure within the heart.

Figure 3B:
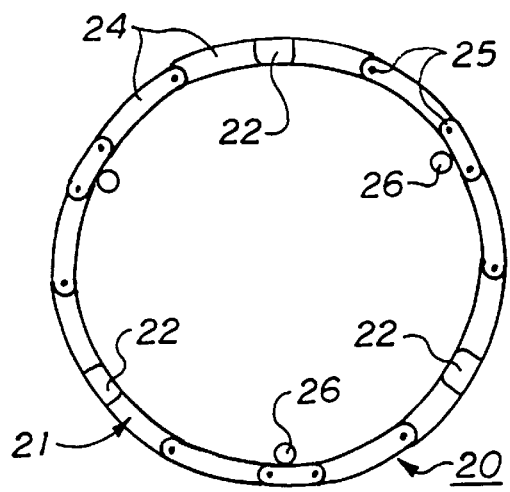
FIG. 3B shows a top plan view of the collapsible inner frame shown in FIG. 3A.
Figure 4A:
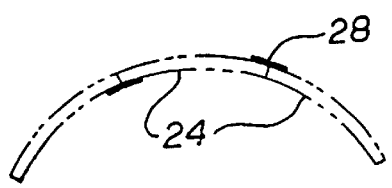
FIG. 4A illustrates a collapsible inner frame in an expanded position, in accordance with an alternative embodiment.
Figure 3C:
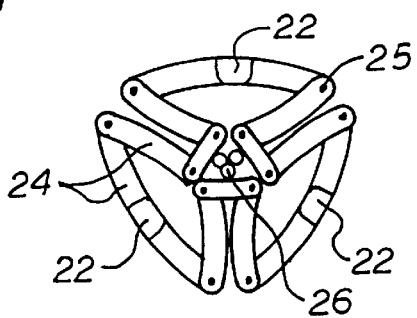
FIG. 3C shows a top plan view of the collapsible inner frame shown in FIG. 3A, in a collapsed position.
Figure 4B:
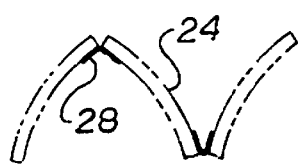
FIG. 4B illustrates the collapsible inner frame of FIG. 4A, in a collapsed position.

Referring now to FIGS. 3A–3B and 4A–4B, there is shown a preferred embodiment of the collapsible valve 20. Collapsible valve 20 is generally comprised of an articulating inner frame 21 having a plurality of projections or stent posts 22, and a plurality of leaflets (not shown). It should be understood that the leaflets are mounted to the stent posts 22 in a manner similar to that shown in FIG. 1, and movable between an occluded position and an open position. The inner frame 21 that supports the plurality of leaflets is formed of a plurality of articulated segments 24 (typically 6 or more segments), that fold together in a way so that the total outer diameter of the inner frame is reduced for insertion, as best seen in FIG. 3C. The articulated segments 24 are typically rigid structures that snap into a locked position as they are completely unfolded during deployment. Articulated segments 24 articulate around pin hinges 25 (FIGS. 3B–3C) or other flexible strips 28 (FIGS. 4A–4B), means that can assure a flexible attachment between any adjacent segments. It will be appreciated that other means for articulating are also suitable, including ball and socket joints.

The process of collapse and expansion involves a "snapping" action that produces some elastic material deformation of the segments 24 and/or the hinges 25 and/or the strips 28, as the segments articulate between their fully expanded configuration and their partially collapsed configuration. This is achieved by means of an interference fit between opposing segments that articulate near each other. The provision for the snapping process is so that once expanded, the inner frame remains expanded under its own internal tension, and does not collapse due to undue internal or external force applied to it during normal activity.

Figure 5:
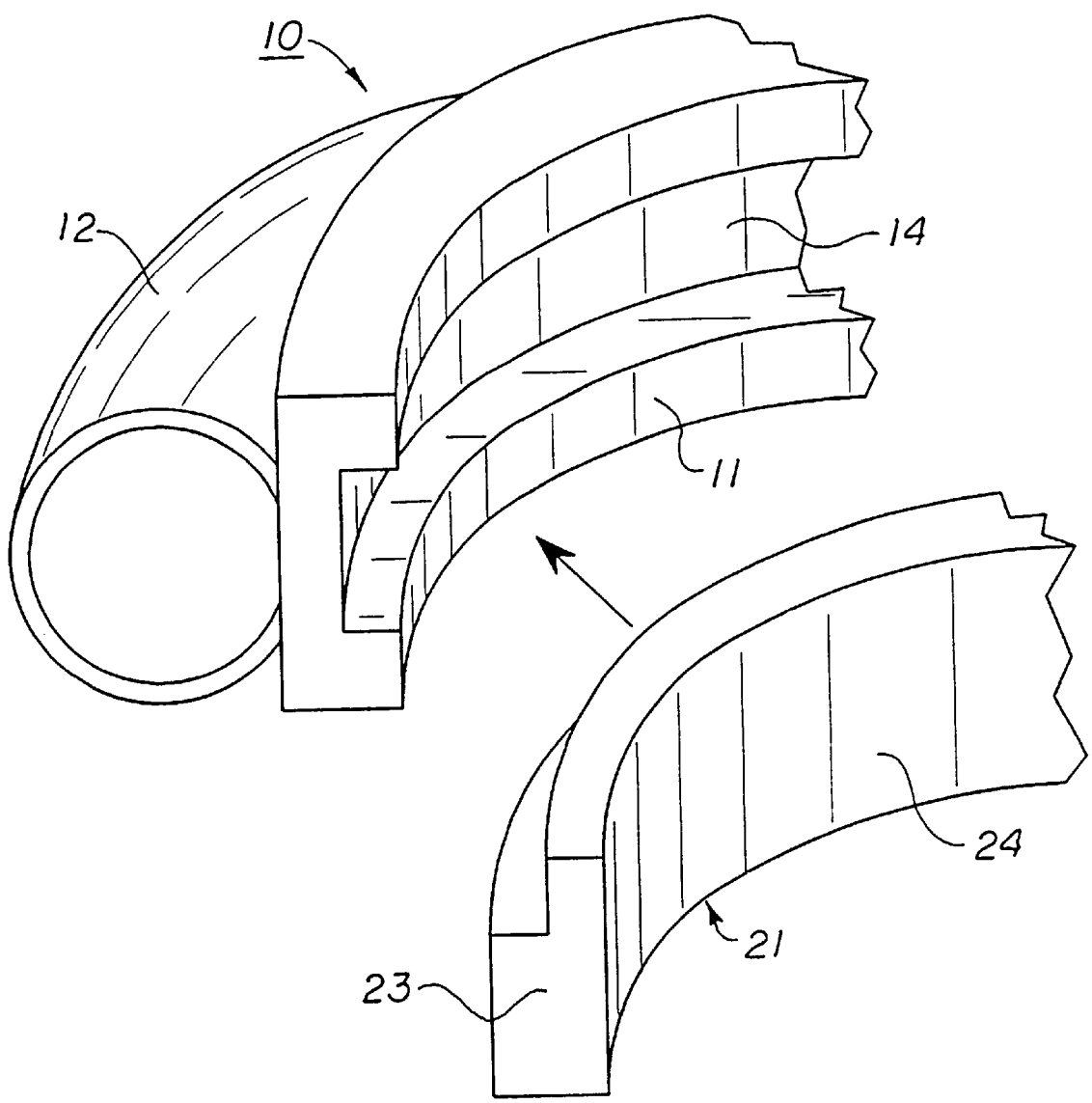
FIG. 5 shows an enlarged partial sectional view of the inner and outer frames, to illustrate the mating surfaces thereof.

Referring now to FIG. 5, the inner frame 21 is held in tight opposition against the rigid ring 11 of the outer frame 10 by means of a generally annular groove 14 on the inner surface of the rigid ring 11, into which each of the articulating segments 24 fit when the inner frame 21 is expanded. Accordingly, annular groove 14 provides a means for interfacing and attaching outer frame 10 with inner frame 11. It will be appreciated that articulated segments 24 include a flange portion 23, which is dimensioned to be received into groove 14. The fit between flange portion 23 of inner frame 21 and groove 14 of rigid ring 11 is such that the collapsible valve 20 cannot be withdrawn from the outer frame 10 when the inner frame 21 is expanded, and can only be withdrawn when the inner frame 21 is collapsed. It should be appreciated that other means for interfacing inner frame 21 with outer frame 10 are also suitable.

II. Collapse and Expansion of the Collapsible Cardiac Valve

Figure 3A:
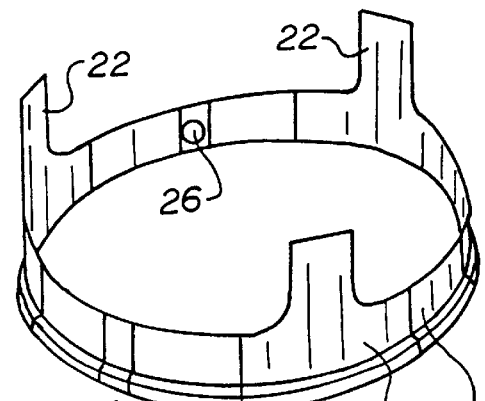
FIG. 3A shows a perspective view of the collapsible inner frame in accordance with a preferred embodiment of the present invention, in an expanded position.
Figure 6A:
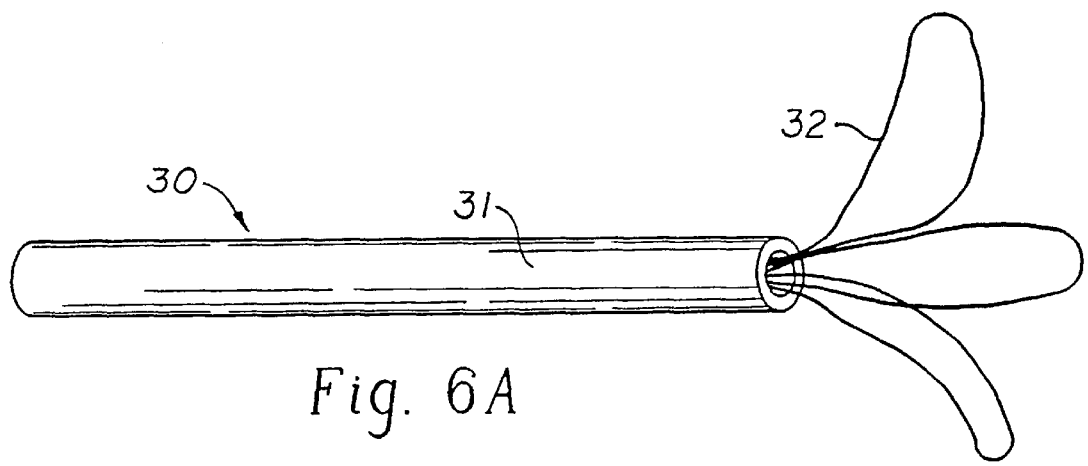
FIG. 6A shows an exemplary embodiment of a valve collapsing catheter.

During most of its useable life span, the collapsible valve 20 remains in its expanded state. The collapse of the inner frame 21 may be carried out with a remote manipulating device, such as valve collapsing catheter 30 (FIG. 6A) that includes one or more snares that grabs onto projections 26 or "handles" formed on the collapsible inner frame 21 (FIGS. 3A–3C). The valve collapsing catheter 30 includes a catheter body 31 and a plurality of cables preformed to conveniently sized loops or snare means 32. The snare means 32 can be extended from the catheter body 31 to preformed shapes, such that they can grab onto the projections 26 of the collapsible inner frame 21. When the snare means 32 are pulled back into the lumen of the catheter body 31, an inward force is achieved, sufficiently strong to "snap" the collapsible inner frame 21 into its collapsed position.

Figure 6B:
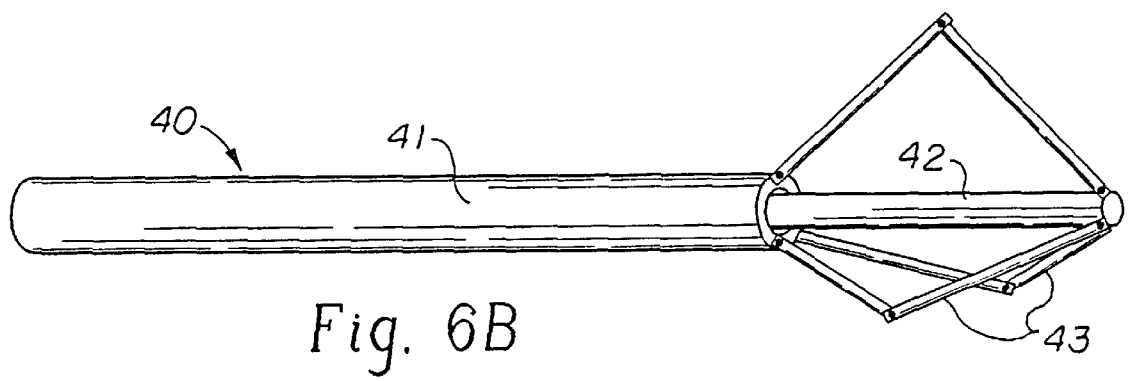
FIGS. 6B and 6C show an exemplary embodiment of a valve expanding catheter.
Figure 6C:
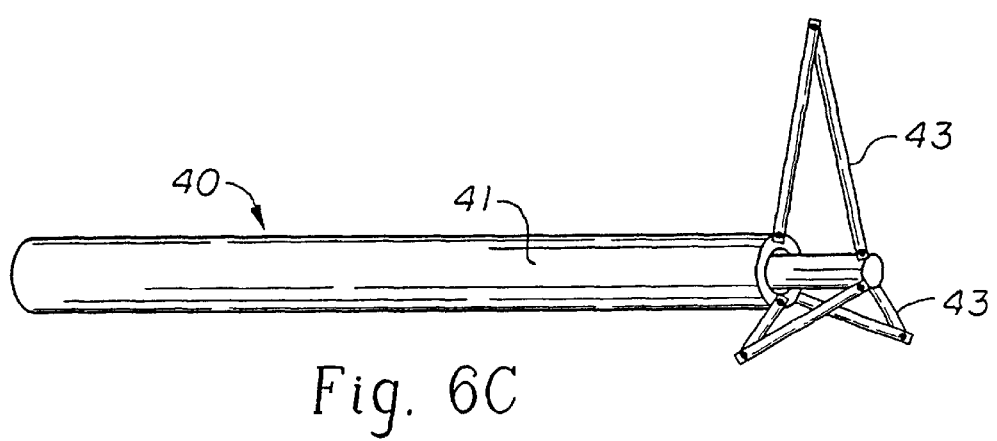
Figure 7E:
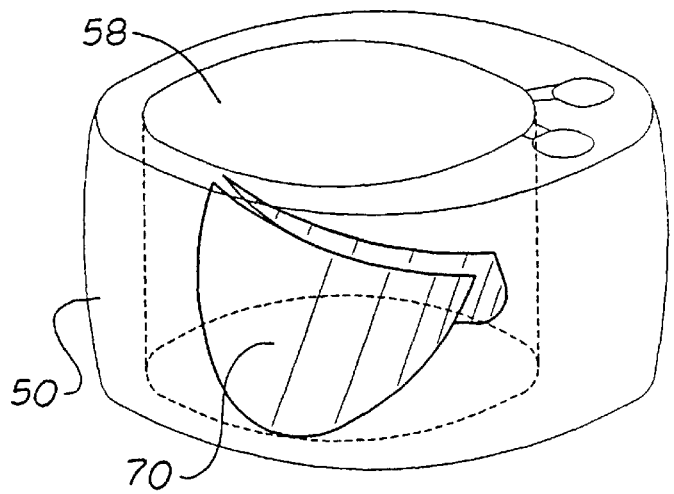
FIG. 7E illustrates a surgical platform having a check valve, in accordance with a preferred embodiment of the present invention.

The process of expansion of the inner frame 21 is opposite to the collapsing process. Referring now to FIGS. 6B and 6C, there is shown a suitable remote manipulating device for expanding the inner frame 21. Valve expanding catheter 40 includes a catheter body 41 and an articulating system 43 at its end that pushes against the projections 26 or some convenient segments 24 in order to expand the inner frame 21 and properly seat it in the outer frame 10. Valve expanding catheter 40 includes an inner rod 42 that slides in when pulled or pushed upon at its proximal end. Articulating system 43 is located at the distal end of inner rod 42, and includes a number of articulating arms or levers that hinge such that they expand when the inner rod 42 is drawn inwards. This action generates an outward push upon the inner frame 21 so that it expands and snaps into place in the rigid ring 11 of the outer frame 10. Because of the fit between the inner frame 21 and the rigid ring 11, the inner frame 21 cannot be separated from the outer frame 10 when expanded, and can only be separated when the inner frame 21 is in the collapsed position. Accordingly, the collapsible valve 20 safely operates when the inner frame 21 is in the expanded position.

III. Intra cardiac Removal and Delivery of Collapsible Cardiac Valve

The system for collapse, removal and delivery of a replacement collapsible valve makes use of novel catheter technologies. A catheter-based valve delivery system must itself be collapsible so that it can be inserted percutaneously, and deliverable by catheter to the appropriate site. In accordance with a preferred embodiment of the present invention, a catheter-based valve delivery system is generally comprised of several catheters or catheter sheaths, that can shuttle components in and out of the body to the desired spot with minimal repositioning.

FIGS. 7A–7E illustrate components of a delivery system, according to a preferred embodiment of the present invention. The distal end of the delivery system is anchored in the ascending aorta, and is referred to herein as the surgical platform 50. All catheters C1, 53 and 57, and other valve manipulation devices have their distal ends anchored within the surgical platform 50, so that they can be stable at their distal end and perform their function with good control and accuracy. The catheters, themselves act as remote manipulators that can be controlled by pull wires, or by means of small actuators controlled electrically or hydraulically that deflect the catheters or in some way change their shape. Since the objectives of some of the catheters is to deliver the collapsible valve 20 and other components from the outside of the patient to the operative site inside the patient, these catheters have an inner lumen through which pull cables and other catheters can slide.

The shuttling of larger objects between the outside world and the surgical platform 50 is achieved by splitting the main guiding catheter 53 along its length to form an elongated slot 55. Accordingly, main guiding catheter 53 acts as a slotted catheter sheath for inner pull cables or an inner catheter 57. Inner catheter 57 has gripping means 54 that project through slot 55 spanning the wall of the main guiding catheter 53. Gripping means 54 attach collapsible valve 20 or other devices to inner catheter 57, and slide along slot 55, as will be explained in detail below. Accordingly, the slotted main guiding catheter 53 and inner catheter 57 provide a "monorail" system that conveniently transports devices in and out of the body by moving them along the length of the main guiding catheter 53.

Since the collapsible valve 20 and other devices may not fit inside a typical catheter, they must be delivered to the operative site along the outside of the main guiding catheter 53. Moreover, the collapsible valve 20 needs to be passed through the surgical platform 50 to the operative site, the slots 55 need to be continuous through the surgical platform 50. Accordingly, the surgical platform 50 is fitted with appropriate similar slots 56 so that the surgical platform 50 does not interfere with the passage of objects along the main guiding catheter 53.

The main guiding catheter 53 is locked in place to the surgical platform 50 by means of a system, such as a twist or snap connector, that lines up the slot 55 of the main guiding catheter 53 with the slot 56 formed in the surgical platform 50. Objects that are passed through the vasculature to the operative site, can be anchored to the inner catheter 57. In this regard, gripping means 54 may include a simple, spring-loaded clamp 59 that is held closed by a conventional coil spring 51 (FIG. 7D). The spring 51 can be opened remotely simply by pushing the inner catheter 57 against the closed end 75 of the main guiding catheter 53. This generates a pushing force on the clamp 59 and allows one of the jaws to rotate, thus opening the clamp and releasing the device. It will be appreciated that gripping means 54 may take other suitable forms.

Figure 8A:
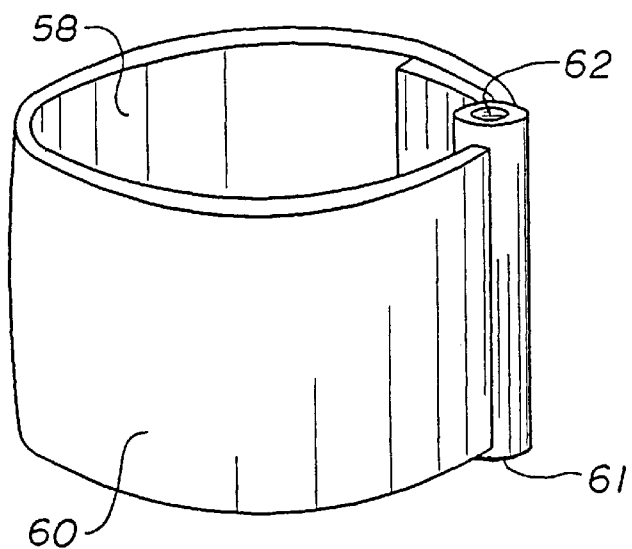
FIG. 8A shows an alternative embodiment of an expandable surgical platform.
Figure 8B:
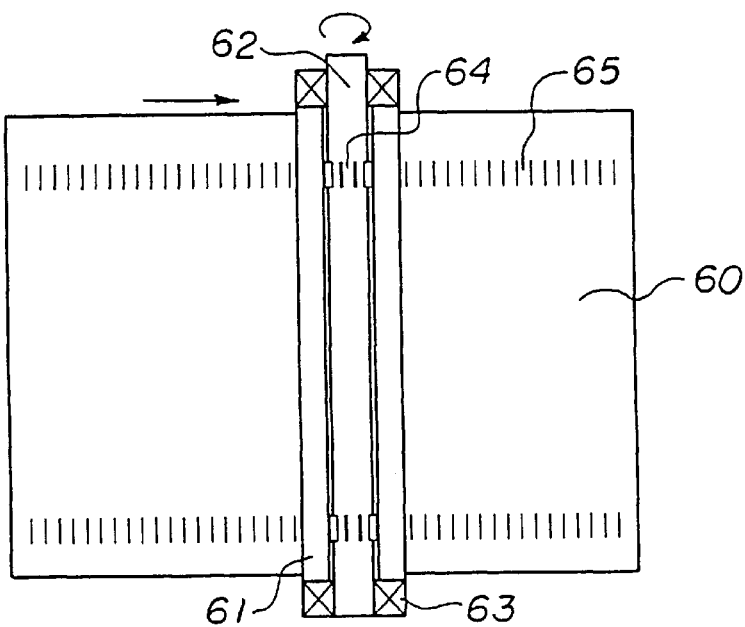
FIG. 8B is a schematic representation illustrating operation of the expandable surgical platform shown in FIG. 8A.

The surgical platform 50 can be fabricated from balloon technology, as shown in FIG. 7A. Alternatively, as shown in FIGS. 8A and 8B, a cylindrical surgical platform 60 can be formed from a wound strip of material that is held in a fitting 61 and unrolls by means of a rotating shaft 62. This means of unwrapping or expanding the wound strip of material to increase its diameter structure, operates in a manner similar to the way that a "hose clamp" reduces its diameter, when being wound up. The rotating shaft 62 can sit suspended within the fitting 61 by means of bushings 63. The shaft 62 can deliver its torque to the wound strip of material through a friction contact, or by means of short teeth or textured bumps 64, that engage with similar depression, pits, or slots 65 on the inner surface of the wound strip of material.

It should be appreciated that the delivery system, and in particular the surgical platforms 50, 60 may also contain an auxiliary synthetic check valve 70 (FIG. 7E) that cyclically opens and closes, replacing the function of the worn out collapsible valve while it is being removed and replaced with a new collapsible valve. The synthetic check valve 70 may be integrated into the lumen 58 of the surgical platform 50. The synthetic check valve 70 is comprised of a one or more flaps of polymer that seal the lumen 58 when the check valve 70 is closed, and move out of the way when the check valve 70 opens passively as blood is ejected from the heart. There is provision made for manually opening the check valve 70 by means of catheters and pull wires, so that larger objects can be passed by this check valve on the way to the operative site. Alternatively, the action of the one-way check valve 70 can be replaced by an occluding balloon that cyclically expands and collapses under external control, and occludes the aorta distal to the surgical platform.

IV. Imaging System for Implantation of Collapsible Cardiac Valve

Complex, remote surgery such as described above, requires a suitable device tracking and visualization system. Conventional MIS procedures can be performed only on organs that do not involve considerable bleeding since the surgeon is oriented and guided only with his own vision, using endoscopic video cameras. Using endoscopes in a bloody environment is not convenient because blood is opaque. Optical visualization and localization inside the beating heart is simply impractical.

Such a system will therefore need real-time, high resolution ultrasound imaging, continuous X-ray fluoroscopy, or some combination of both. Real-time open magnet MRI is also an option, but the need for high strength metallic instruments in this system makes MRI unlikely. X-ray imaging is undesirable because of the harmful radiation, and ultrasound does not currently have sufficient spatial resolution when operated in 3-D mode and is unlikely to in the near future. Ultrasound imaging is also susceptible to shadowing from dense, metallic objects. Innovative imaging modalities alone, may not be sufficient for properly guiding the valve replacement procedure. A 3-D visualization system, that integrates multiple imaging modalities and real time device tracking, is therefore most suitable. For instance, an ultrasonic catheter and device tracking system, analogous to that described in U.S. Pat. No. 5,515,853 (incorporated herein by reference), would be very appropriate, if linked to a powerful 3-D graphics engine that can simulate the position and movement of the various objects as they are manipulated inside the patient. Another device tracking system that could be used would employ electromagnetic localizer technology, such as that described in U.S. Pat. No. 5,546,951 (incorporated herein by reference). Other electrical, magnetic or image based localizer system can be used with similar function. To provide additional information, numerous images obtained simultaneously using ultrasound, X-ray or other imaging modalities could be integrated into this viewing environment, as described in U.S. Pat. No. 5,817,022 (incorporated herein by reference), to provide additional feedback regarding the true position of the objects.

V. Other uses of Device Delivery System.

Figure 9B:
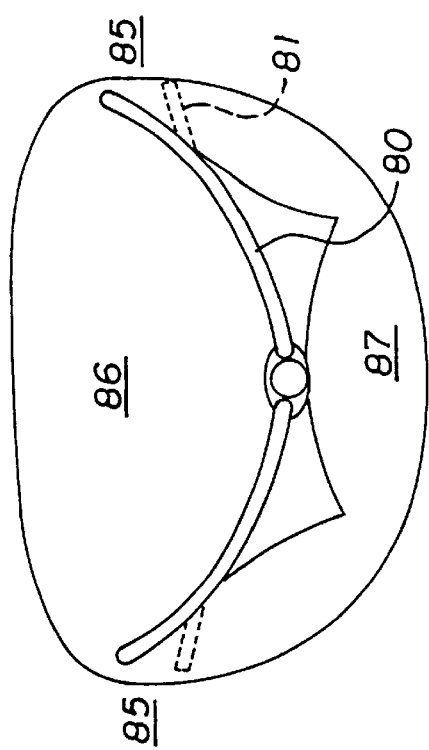
FIG. 9B illustrates a top view of the cardiac anatomic site shown in FIG. 9A.
Figure 9C:
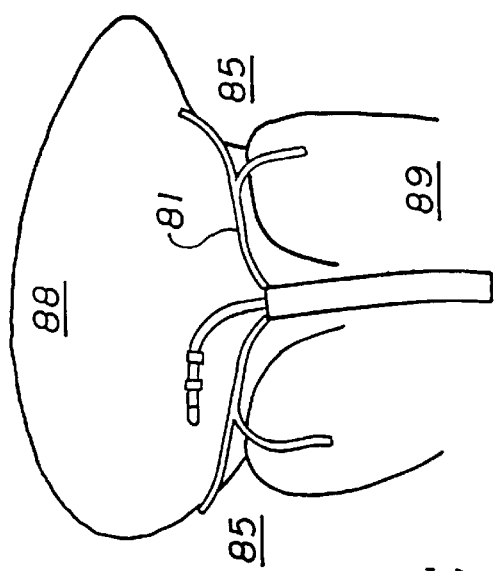
FIG. 9C is a simplified enlarged front view of the cardiac anatomic site shown in FIG. 9A.
Figure 9A:
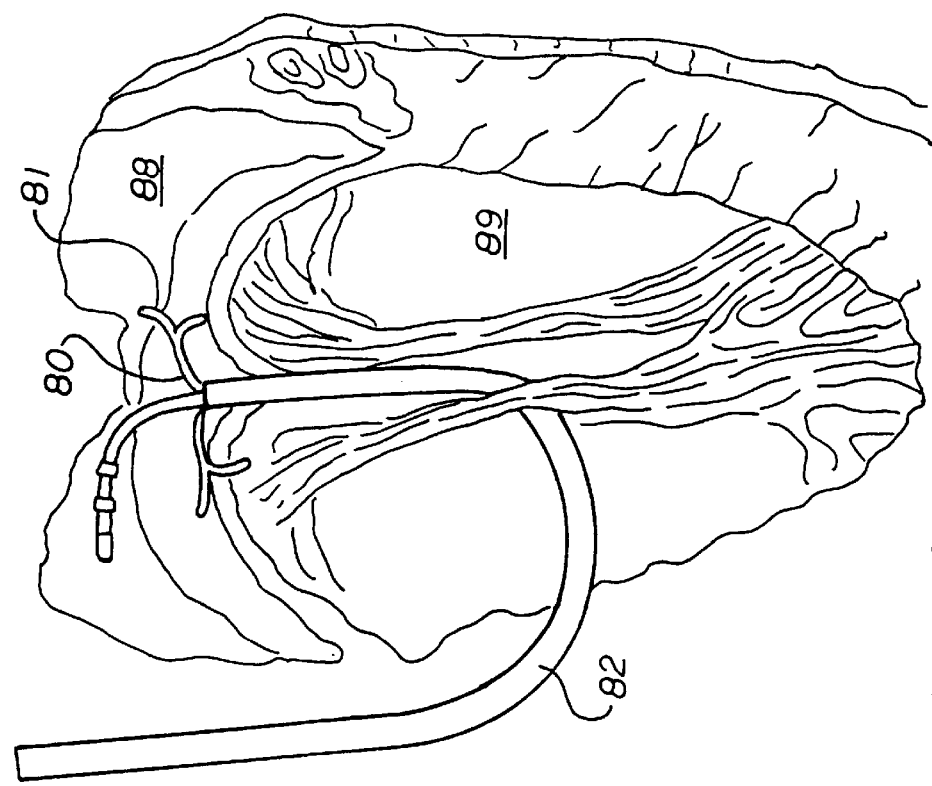
FIG. 9A illustrates a front view of the cardiac anatomic site.

There is a growing number of surgical and therapeutic procedures that involve the delivery of a device or multiple devices to the inside of a body to a site of surgery or device deployment. To date, all of these systems employed a conventional catheter without the longitudinal split, and without the use of a surgical platform. Use of the present invention: (i) enables the delivery of larger devices to the target site by the use of smaller catheters, and (ii) stabilizes the distal end of the catheter for much more precise, more controllable catheter-based procedures. Such a surgical platform can be used for ablation procedures within the ventricles and the atria by better stabilizing the catheters, for the delivery of larger endovascular prostheses or occluding devices to stop internal bleeding, such as in cirrhotic liver vessels or ventricular-septal defects. The surgical platforms for such applications do not need to incorporate internal valves and can therefore be simplified into baskets or cages or articulating structures that simply lodge themselves against the appropriate anatomy, as shown in FIGS. 9A–9C, in the case for atrial access. In this embodiment, the surgical platform 80 includes forked projections 81 that slide out of a main catheter 82 and lodge themselves against appropriate cardiac anatomy, such as the commissures of the mitral valve 85. The "commissure" is an anatomic site, defined as the spot where the anterior leaflet 86 meets the posterior leaflet 87. These commissures are also located between the atrium 88 and the ventricle 89, which in themselves provide walls or surfaces against which the projections 81 can be anchored.

The present invention has been described with reference to a preferred embodiment. Obviously, it will be appreciated by those skilled in the art that various additions, modifications, deletions and alterations will occur to others upon a reading and understanding of this specification, and may be made to such preferred embodiments without departing from the spirit and scope of the invention. Accordingly, it is intended that all such modifications and alterations be included within the scope of the invention as defined in the following claims.

Having thus described the invention, it is now claimed:

1. A heart valve system comprising:

first frame means attachable to tissue; and second frame means engageable and disengageable with said first frame means, wherein said second frame means includes a plurality of articulated segments, said second frame means movable between an expanded position to engage with the first frame means and a collapsed position to disengage from the first frame means.

2. A heart valve system according to claim 1, wherein said second frame means supports occluding means movable between an occluded position and an open position.

3. A heart valve system according to claim 2, wherein said occluding means includes at least one leaflet occluder.

4. A heart valve system according to claim 3, wherein said leaflet occluder includes biological tissue.

5. A heart valve system according to claim 3, wherein said leaflet occluder includes bovine pericardium.

6. A heart valve system according to claim 1, wherein said articulated segments are rigid.

7. A heart valve system according to claim 1, wherein at least one of said plurality of articulated segments includes a projection member for facilitating the movement of said second frame means between said expanded position and said collapsed position.

8. A heart valve system according to claim 1, wherein said plurality of articulated segments define a first outer diameter when said second frame means is moved to said collapsed position, and define a second outer diameter when said second frame means is moved to said expanded position, said first outer diameter being less than said second outer diameter.

9. A heart valve system according to claim 1, wherein said plurality of articulated segments articulate by pin joints.

10. A heart valve system according to claim 1, wherein said articulated segments articulate by flexible strips.

11. A heart valve system according to claim 1, wherein said articulated segments articulate by ball and socket joints.

12. A heart valve system according to claim 1, wherein said first frame means includes a rigid member having interface means for reversibly engaging said second frame means therewith.

13. A heart valve system according to claim 12, wherein said interface means includes a groove member for receiving at least a portion of said second frame means when said second frame means is in the expanded position.

14. A heart valve system according to claim 1, wherein said first frame means includes attachment means for attaching said first frame means to said tissue.

15. A heart valve system according to claim 14, wherein said attachment means includes a sewing ring.

16. A valve system comprising:

first frame means attachable to bodily tissue;

second frame means engageable and disengageable with said first frame means, wherein said second frame means is movable between an expanded position to engage with the first frame means, said a collapsed position to disengage from the first frame means; and valve means supported by said second frame means.

17. A valve system according to claim 16, wherein said valve means includes biological tissue.

* * * * *